Figure 1:
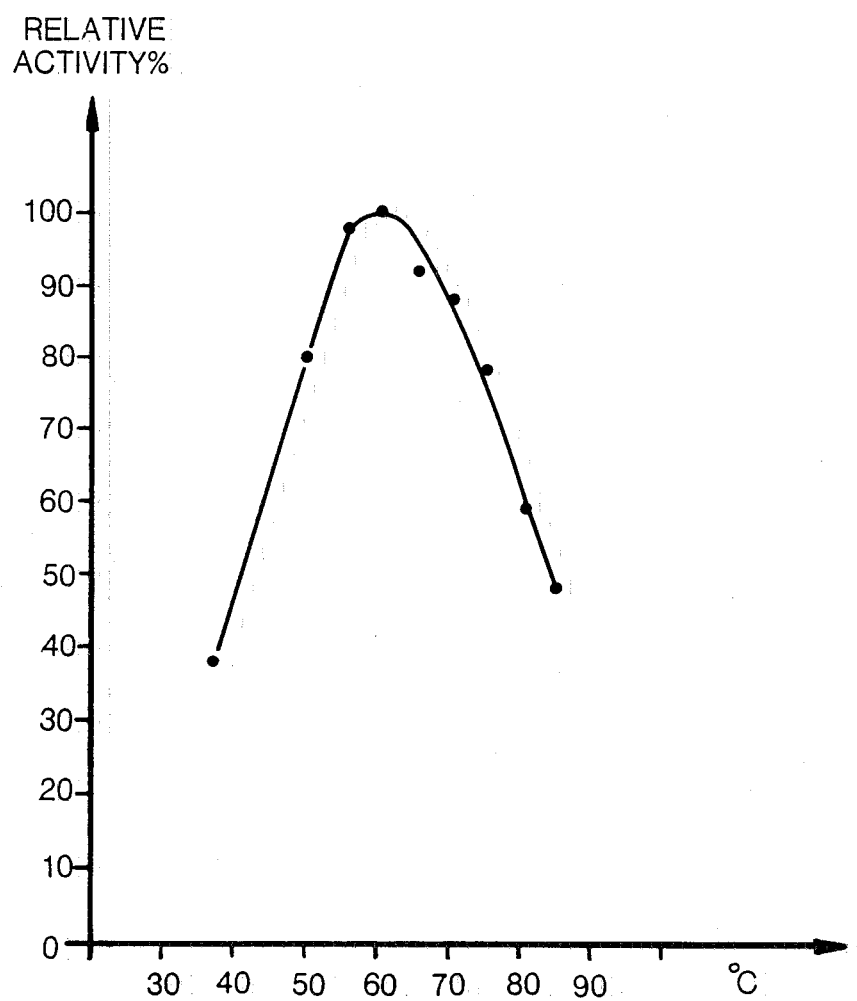

United States Patent [19]

Diderichsen et al.

[11] Patent Number: 4,598,048
[45] Date of Patent: Jul. 1, 1986

[54] PREPARATION OF A MALTOGENIC AMYLASE ENZYME

[75] Inventors: Boerge K. Diderichsen, Hellerup; Lars Christiansen, Lyngby, both of Denmark

[73] Assignee: Novo Industri A/S, Denmark

[21] Appl. No.: 591,461

[22] Filed: Mar. 20, 1984

[30] Foreign Application Priority Data

Mar. 25, 1983 [DK] Denmark ............................ 1359/83

[51] Int. Cl.$^4$ ........................ C12N 15/00; C12N 9/26
[52] U.S. Cl. ................................ 435/172.3; 435/201; 935/14; 935/27; 935/56
[58] Field of Search ..................... 435/95, 201, 172.3; 935/14

[56] References Cited

U.S. PATENT DOCUMENTS 4,469,791 9/1984 Colson et al. ...................... 935/14 X
4,493,893 1/1985 Mielenz et al. ...................... 435/201

*Primary Examiner*—Lionel M. Shapiro
*Attorney, Agent, or Firm*—Fidelman, Wolffe & Waldron

[57] ABSTRACT

A maltogenic amylase enzyme with improved thermostability, which can be produced by cultivating Bacillus strain NCIB 11837 belonging to the *Bacillus stearothermophilus* complex, is made by cultivation of a host microorganism transformed with the gene coding for the maltogenic amylase enzyme.

14 Claims, 3 Drawing Figures

4,598,048

PREPARATION OF A MALTOGENIC AMYLASE ENZYME

This invention concerns the process for preparation of a maltogenic amylase.

BACKGROUND OF THE INVENTION

β-amylases are maltogenic exo-amylases which hydrolyse α-1,4-glycosidic bonds from the non-reducing ends of amylose, amylopectin, or glycogen to produce the β-form of maltose. The β-form of maltose will isomerize spontaneously in aqueous solutions to a mixture of the α- and β-form.

β-amylases may be used to produce maltose containing syrups of use in the confectionery-, baking-, and brewing industries.

β-amylases have been isolated from various plants and microorganisms (W. M. Fogarty and C. T. Kelly, Progress in Industrial Microbiology, vol. 15, p. 112-115, 1979). The β-amylases known from plants (barley, sweet potato, and soy beans) and from the Bacillus species *B. mycoides*, *B. megaterium*, and *B. polymyxa* are all enzymes whose activity is inhibited by sulphydryl reagents, such as PCMB (para-chloromecuribenzoate) thus indicating that the active site involves an SH-group.

Hitherto only one β-amylase has been described which is not inhibited by PCMB, namely a β-amylase produced by *Bacillus circulans* (U.S. Pat. No. 4,001,136). The *B. circulans* β-amylase is more thermostable than the above mentioned β-amylases. However, it is rapidly inactivated at and above 65° C.

In a process for the production of maltose wherein starch in an aqueous medium is hydrolyzed by a β-amylase it is, however, advantageous to use a process temperature of about 65°-70° C. to inhibit retrogradation and to avoid microbial infections.

Therefore, the above mentioned *Bacillus circulans* β-amylase is less than well suited for commercial use at about 65°-70° C. because of too rigid deactivation.

In U.S. Pat. No. 3.804.715 is disclosed a heat resistant β-amylase which is extracted from wheat bran as described in British Pat. No. 1.130.398. The β-amylase is, however, less attractive in a commercial process as compared with an enzyme derived from a bacterial source because the latter can be produced on a large scale at relatively low costs compared to that of a β-amylase of plant origin.

Therefore, there exists a need for an effective microbial maltogenic amylase preparation which is sufficiently thermostable to be employed at 65°-70° C. for extended periods of time to allow hydrolysis of the starch in an economical way.

It is an object of the present invention to furnish a microbial maltogenic amylase which apart from not being inactivated by sulphydryl reagents as PCMB has a high temperature stability in commercially feasible yields.

The present invention is based upon the discovery that high yields of an extracellular maltogenic enzyme (C599 amylase) having such properties can be obtained by cultivation of a transformed *B. sutilis* strain. The parent strain Bacillus strain NCIB 11837 for the C599 amylase is a poor producer of the maltogenic enzyme.

Figure 2:
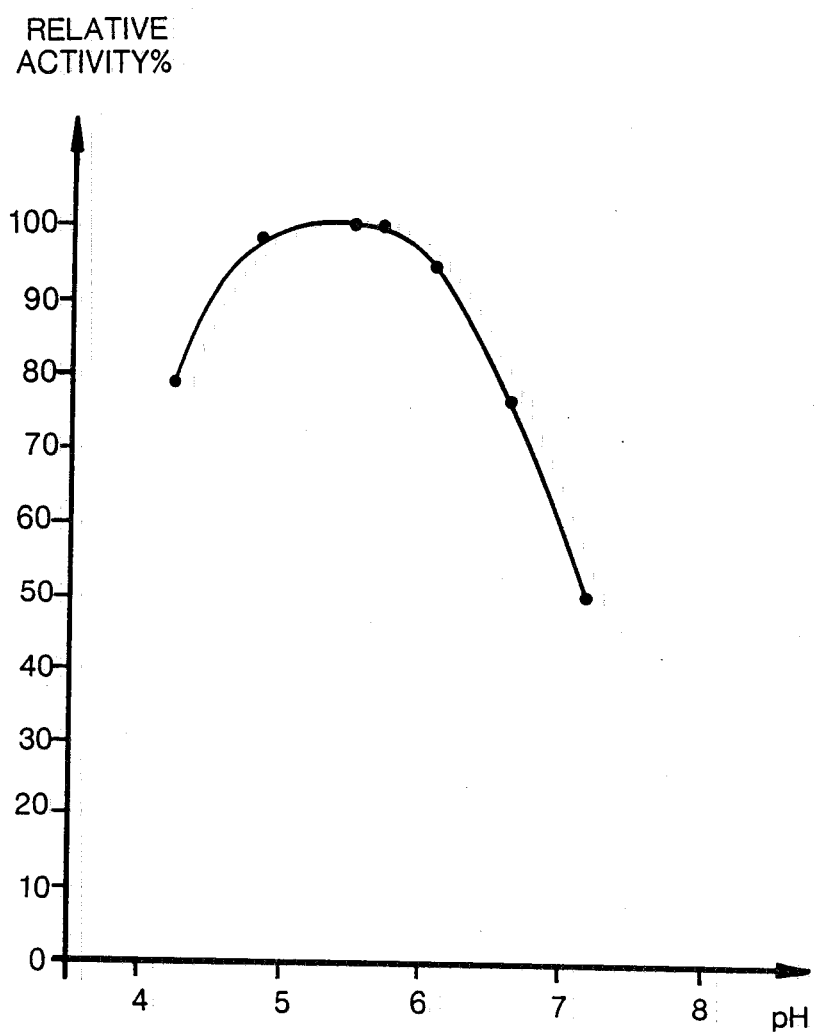
Figure 3:
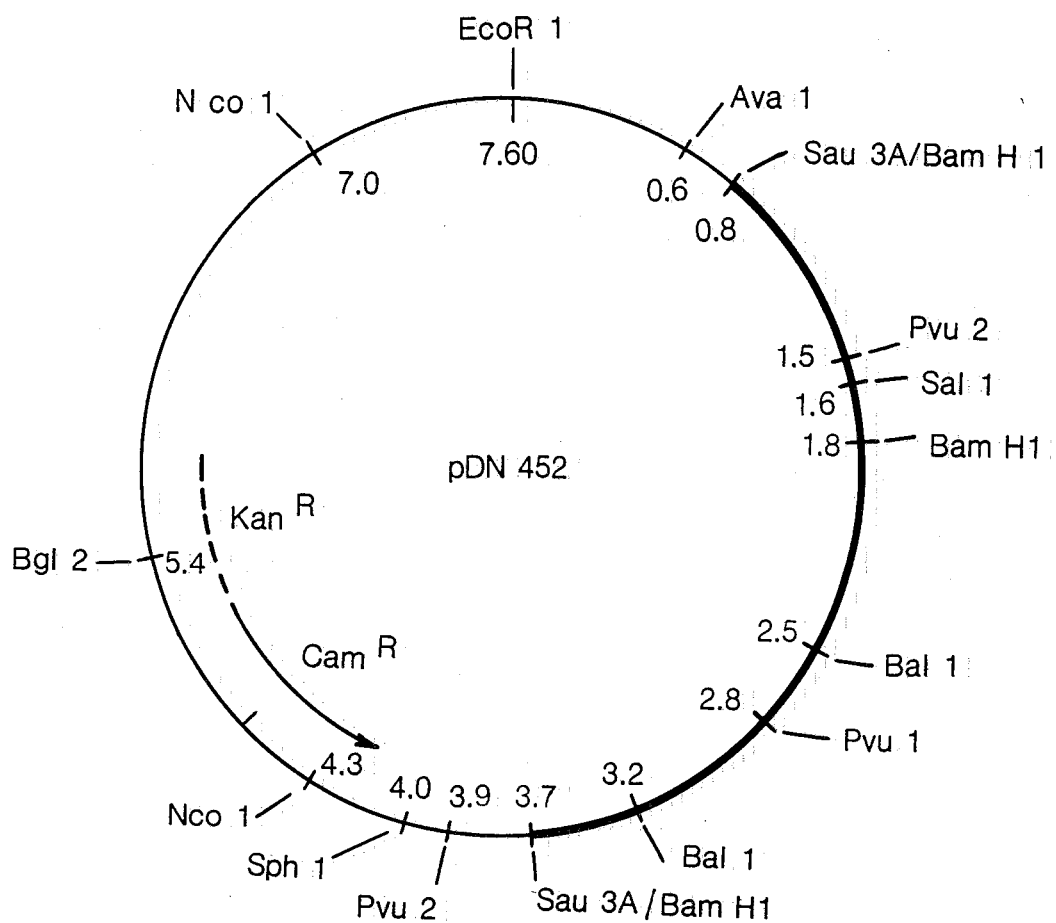

For better understanding of the invention herein and the description which follows, attention is directed to the attached drawing wherein:

FIG. 1 is a plot of relative activity of the maltogenic enzyme against temperature;
FIG. 2 is a plot of relative activity against pH; and
FIG. 3 depicts the restriction endonuclease cleavage map for the novel plasmid pDN452 of this invention.

SUMMARY OF THE INVENTION

The maltogenic amylase enzyme product C599 amylase comprises a thermostable maltogenic amylase having the following characteristics:

(a) it is obtainable by cultivation in a suitable nutrient medium of Bacillus strain C599 NCIB 11837.
(b) it exhibits the enzyme chemical and immunological properties of the maltogenic amylase derived from the Bacillus strain C599,
(c) its activity optimum measured at 30 min reaction time in acetate buffer (0.1M) at pH 5.5 is about 60° C.,
(d) its pH optimum is at 30 min reaction time in the range of 4.5-6 as determined in a MC Ilvaine buffer at about 60° C. and
(e) it has a residual activity after 60 minutes at 70° C. in acetate buffer (0.1M) at pH 5.5 of at least 75%.

The maltogenic amylase product may be in solid or liquid form. Solid forms will generally have an activity of 500-25000 U (as hereinafter defined) per gram.

By means of DNA recombinant technique the gene coding for the thermostable maltogenic amylase has been transferred into another microorganism which produces, under appropriate conditions of cultivation, substantially greater amounts of the maltogenic amylase than are produced by the donor parent strain microorganism (C599).

The present invention accordingly provides a method of preparing a maltogenic amylase enzyme product by transforming a suitable host microorganism with a recombinant plasmid containing a gene coding for the maltogenic, thermostable amylase and cultivating the transformed microorganism in a suitable nutrient medium containing carbon and nitrogen sources and inorganic salts followed by recovery of said maltogenic amylase enzyme product.

According to a further aspect, the present invention provides a method of producing a recombinant plasmid containing the gene coding for the thermostable maltogenic amylase which method comprises cutting with an appropriate restriction enzyme chromosomal DNA from a donor microorganism productive of amylase to obtain a linear DNA-sequence containing the amylase-coding gene, cutting a suitable vector to obtain a second linear DNA-sequence and ligating the two linear DNA-sequences to obtain a recombinant plasmid containing the amylase gene.

The vector, preferably an *E. coli* plasmid, is cut with an appropriate restriction enzyme that will give linear DNA with ends that can be joined to ends of the fragments of donor DNA.

Ligation of the two linear sources of DNA-sequences is accomplished by means of a ligase using techniques well known in the art.

According to a preferred embodiment of the present invention the host microorganism is selected from the Bacillus group, preferably *B. subtilis*.

Transformation of the host microorganism is also accomplished by well known methods including transforming of the recombinant plasmid into *E. coli* cells, identifying starch degrading transformants and subcloning the recombinant plasmid from such Amy+ transformants into the chosen host microorganism.

The host microorganism (which preferably does not display amylase activity) can upon acquisition of the said recombinant plasmid produce the novel maltogenic amylase when cultured on an appropriate culture medium. The amylase is secreted into the growth medium, thus providing a simple enzyme recovery step.

The present invention also provides a new recombinant plasmid, pDN452, containing a gene coding for the said amylase which plasmid is prepared by cleaving chromosomal DNA from Bacillus C599 with the restriction enzyme MboI, isolating DNA-fragments in the range of 4–12 kb (kilobase pairs), ligating with E. coli plasmid pACYC184, which has been cut with restriction enzyme BamHI, transforming into E. coli cells, identifying the starch degrading transformants which harbour plasmids containing the amylase gene, cutting said plasmids with a restriction enzyme Sau3AI, ligating the DNA-fragment expressing amylase activity with plasmid pBD64 which has been cut with the restriction enzyme BamHI and transforming the new recombinant plasmid into B. subtilis.

FIG. 3 depicts the restriction endo-nuclease cleavage map for this novel plasmid pDN452. The novel plasmid is a 7.6 kb hybrid plasmid which comprises the nucleotide sequence of pBD64 and inserted at the BamHI site of this plasmid the DNA sequence from Bacillus C599 coding for the said amylase.

According to a further aspect the present invention provides a process for the production of high purity maltose syrups wherein starch is treated with the novel maltogenic amylase enzyme product in an aqueous medium.

Tests have shown that the novel maltogenic amylase enzyme product is suitable for the production of maltose and high maltose syrups. Such products are of considerable interest by the production of certain confectioneries because of the low hygroscoposity, low viscosity, good heat stability and mild, not too sweet taste of maltose.

Although the enzyme of this invention in many respects reacts like the known β-amylases it differs therefrom in several essentials as will appear in the following detailed description and, consequently, the enzyme is characterized as a maltogenic amylase, rather than a β-amylase.

The enzyme migrates at SDS-polyacrylamid gelelectrophoresis as a single band indicating a molecular weight of about 70,000 Dalton. The isoelectric point determined by thin layer gelelectrofocusing is 8.5.

C599 amylase hydrolyzes amylopectin, glycogen, and amylose, maltose constituting a substantial part of the reaction products. Glucose is generated in small amounts corresponding to 1–10% of the maltose formed.

From branched polysaccharides, such as amylopectin and glycogen C599 amylase forms limit dextrins, which can be hydrolyzed by glycoamylase.

Sulphydryl reagents, such as para-chlor-merruribenzoate and chelating agents, such as EDTA do not have any influence on the enzyme activity.

C599 maltogenic amylase differs from the known β-amylases in the following respects:

1. It hydrolyzes Schardinger-cyclodextrins quantitatively. Schardinger-β-cyclodextrin is hydrolyzed into maltose+glucose in a molar ratio of 3:1, whereas α-cyclodextrin is hydrolyzed into maltose+glucose in a molar ratio of 10:1. $^1$HNMR spectral analysis of α-cyclo dextrins incubated with the maltogenic amylase shows the initial formation of α-maltose as the first main product.
2. Maltotriose is quantitatively cleaved into equimolecular amounts of maltose and glucose. $^1$HNMR spectral analysis of maltotriose incubated with the maltogenic amylase shows that the hydrolysis product is α-maltose+glucose.
3. It is stable in buffer at 70° C., and
4. the limit dextrins of C599 maltogenic amylase do not form coloured complexes with $I_2$-KI-reagens.

Accordingly the maltogenic amylase is an exoenzyme which attacks the α-1,4-glycosidic bonds the main hydrolysis product being α-maltose.

The ability of the maltogenic amylase to cleave maltotriose present in the known maltose syrups quantitatively into maltose and glucose thereby increasing the maltose yield is noteworthy as lately there has been an increasing interest in high maltose syrups containing more than 80% maltose.

For the description of the parent microorganism reference is made to copending application Ser. No. 591,460 filed concurrently herewith.

Determination of Enzyme Activity

One maltogenic amylase unit (U) is defined as the amount of enzyme which under standard conditions (temperature 60° C., pH 5.5, and reaction time 30 minutes) produces reducing sugar corresponding to 1 μmol maltose per minute.

A 0.5% soluble starch (supplied by Merck) in 0.1M acetate buffer or 0.05M phosphate buffer (pH 5) is incubated with 1 ml of the enzyme dissolved in deionized water containing 0.1–0.2 U per ml. The reaction is stopped after 30 minutes by addition of 4 ml 0.5N NaOH.

The content of reducing sugar is then determined by means of the Somogyi method (Somogyi: J.Biol.Chem., 153 p. 375–80 (1944)).

An alternative way of determining the enzyme activity is based upon the capability of the maltogenic amylase to quantitatively cleave maltotriose into equimolar amounts of maltose and glucose.

One maltogenic amylase NOVO unit (MANU) is defined as the amount of enzyme which under standard conditions cleaves 1 μmol maltotriose per minute. The enzyme reaction is stopped by shifting pH to about 11. The glucose formed is by means of glucose dehydrogenase (Merck, GlucDH) converted into gluconolactone under formation of NADH. The amount of NADH formed is measured by colorimetric determination at 340 nm.

Standard conditions:
Temperature 37° C.±0.05° C.
pH 5.0
Incubation time 30 min.

REAGENTS 1. 0.1M citrate buffer, pH 5.0

5.255 g citric acid ($C_6H_8O_7$, $H_2O$) is dissolved in about 200 ml demineralized water and pH is adjusted to 5.0 with 4.0/1.0N NaOH. Demineralized water is added up to 250 ml and pH is controlled. The buffer solution may be stored for one week in the refrigerator (pH must be checked before use) but is preferably prepared each test day.

2. Maltotriose substrate 20 mg/ml

To 500 (1000) mg maltotriose (Sigma M 8378) is added citrate buffer (reagent 1) up to 25 (50) ml. To be prepared each test day.

3. GlucDH reagent

Enzyme mixture, Merck No. 14055 flask "1" and "2", is filled up with buffer solution, Merck No. 14051. After 15 min. standing the flask contents are transferred to a 500 ml measuring flask containing about 200 ml buffer (Merck No. 14051) and additional buffer is added up to 500 ml. Stable 14 days in refrigerator.

4. Stopreagent 0.06N NaOH.

GLUCOSE STANDARD CURVE 1.6 g glucose is dissolved in 1000 ml demineralized water aliquots of 1.0, 2.0, 4.0, 6.0 and 10.0 ml are diluted with demineralized water up to 100 ml. The obtained five standard solutions have a glucose concentrations of 88.8, 177.6, 355.2, 532.9 and 888.1 $\mu$mol/liter respectively.

The glucose standard curve is made by mixing 2.0 ml of the above glucose standard solutions with 3.0 ml GlucDH reagent and incubating for 30 min. at ambient temperature whereafter $OD_{340}$ is measured. As blank a sample with demineralized water instead of glucose is used.

ENZYME TEST SAMPLE

The test samples are diluted with demineralized water so that the end dilution is within the interval covered by the standard curve.

ASSAY

To 500 $\mu$l enzyme (preheated to 37° C.) was added 500 $\mu$l maltotriose substrate (preheated to 37° C. and the mixture was after careful mixing placed on a water bath (37° C.). After 30 min reaction time the test tube was removed from the water bath and 1000 $\mu$l stop reagent was added 3.0 ml GluDH reagent was then added and $OD_{340}$ was measured after 30 min standing at ambient temperature.

As blank a sample containing enzyme, stop reagent and maltotriose substrate was used. The maltotriose substrate was not added until immediately after the stop reagent.

ENZYME PREPARATION

A Bacillus strain either the parent strain C599 or a transformed *B. subtilis* capable of producing the maltogenic amylase is usually propagated on a solid substrate prior to its cultivation under aerobic conditions in a suitable fermentation medium. Both media contain assimilable sources of carbon and nitrogen besides inorganic salts optionally together with growth promoting nutrients, such as yeast extract. The fermentation is typically conducted at 50°–55° C. and at a pH of 6.5 and preferably kept approximately constant by automatic means. The enzyme is excreted into the medium.

The ensuing fermentation broth may be freed of bacterial cells, debris therefrom together with other solids, for example by filtration. The supernatant containing the enzyme may be further clarified, for example by filtration or centrifugation, and then concentrated as required, for example by ultrafiltration or in an evaporator under reduced pressure to give a concentrate which, if desired, may be taken to dryness, for example by lyophilization or spray-drying. Typically, the resulting crude enzyme product exhibits an activity in the range of 500–25,000 U per gram.

PURIFICATION OF ENZYME

The maltogenic amylase can be purified from a batch fermentation culture broth as follows:

250 liters of culture broth with an enzyme activity of 4 E per ml is filtered and the filtrate is ultrafiltered, germ filtered, and freeze-dried. 193 g of freeze-dried powder are obtained having an activity of 2400 E per g corresponding to 47% of the original activity.

The powder is dissolved in 15 mM acetate buffer, pH 5.0 and dialysed against 15 mM acetate buffer pH 5.0 until the conductivity is about 1 mS. The dialyzate is then applied to a cation exchanger CM-sepharose Cl-6B which has been equilibrated with the same buffer. The amylase passes through the column whereas 60% of the remaining proteins is withheld by the ion-exchanger.

The pH of the effluent from this column is adjusted to 4.0 with acetic acid and the eluate is subsequently applied to a CM-sepharose Cl-6B column equilibrated with 15 mM acetate buffer pH 4.0. Under these circumstances the amylase is adsorbed by the ion-exchanger. The enzyme is then eluated with acetate buffer of pH 4.0 with increasing ionic strength. The enzyme activity in the eluate follows the protein content in a symmetrical peak. The peak material shows a single sharp protein band by SDS-polyacrylamid gel electrophoresis. The MW is about 70,000 Dalton. pI is 8.5 as determined by iso-electric focusing. The specific activity is 325 MANU/mg protein of the crystallized, redissolved and freeze dried product.

IMMUNOLOGICAL PROPERTIES

Monospecific antiserum was generated by immunizing rabbits with purified maltogenic amylase according to the method described by N. H. Axelsen et al., A Manual of Quantitative Immunoelectrophoresis (Oslo 1973) chapter 23.

Crossed immunoelectrophoresis according to the same authors of crude C599 amylase against this serum gave a single peak of immunoprecipitate confirming the monospecificity of the antiserum.

ENZYME CHEMICAL PROPERTIES

The dependence of the activity of the maltogenic amylase on pH and temperature was determined by the method described above using a reaction mixture in which pH and temperature were adjusted to predetermined values.

Reference is again made to the attached drawings in which

FIG. 1 graphically illustrates the relative activity plotted against temperature (substrate 4% soluble starch, pH 5.5 (0.1M acetate), 30 minutes reaction time) and FIG. 2 graphically illustrates the relative activity plotted against pH (temp. 60° C., substrate 2% soluble starch, 30 minutes reaction time, MC Ilvaine buffer).

It appears from the drawings that C599 maltogenic amylase has an activity optimum at pH 5.5 of about 60° C. and that its pH optimum is in the range of 4.5–6.0. More than 50% of the maximum activity is still found at 80° C.

In order to determine the thermostability of the maltogenic enzyme the enzyme preparation, 1500 E/g, was mixed with 0.1M acetate buffer (150 mg/ml) of pH 5.5 at a temperature of 50° C., 60° C., and 70° C., respectively. The residual amylase activity was determined by the method described above. The results are presented in the following table:

TABLE I

| Temperature | Time min. | Percent residual activity |
|---|---|---|
| 50 | 0 | 100 |
| | 15 | 100 |
| | 30 | 100 |
| | 60 | 100 |
| 60 | 0 | 100 |
| | 15 | 100 |
| | 30 | 100 |
| | 60 | 100 |
| 70 | 0 | 100 |
| | 15 | 90 |
| | 30 | 80 |
| | 60 | 75 |

After 60 minutes at 70° C. 75% of the enzyme activity is retained. None of the known β-amylases exhibits such a good thermostability.

The influence of a variety of agents on the activity of the maltogenic amylase of the present invention is shown in the following Table II.

TABLE II

| | Inhibition of C599-amylase |
|---|---|
| Inhibitors | Residual activity after 60 min. at room temperature, % |
| None | 100 |
| PCMB, 1 mM | 92 |
| EDTA, 1 mM | 104 |
| Schardinger-α-cyclo-dextrin, 1% | 109 |
| Schardinger-β-cyclo-dextrin, 1% | 107 |
| $CaCl_2$ 1 mM | 85 |
| 10 mM | 73 |
| KCl 1 mM | 95 |
| 10 mM | 94 |
| $MgCl_2$ 1 mM | 95 |
| 10 mM | 93 |
| $CoCl_2$ 1 mM | 91 |
| 10 mM | 44 |
| $FeCl_2$ 1 mM | 96 |
| 10 mM | 74 |
| $MnCl_2$ 1 mM | 78 |
| 10 mM | 52 |
| NaCl 1 mM | 98 |
| 10 mM | 96 |
| $CuCl_2$ 1 mM | 10 |
| 10 mM | 1 |
| $ZnCl_2$ 1 mM | 51 |
| 10 mM | 15 |
| $BaCl_2$ 1 mM | 98 |
| 10 mM | 92 |
| $AlCl_3$ 1 mM | 98 |
| 10 mM | 84 |
| $HgCl_2$ 0.1 mM | 3 |
| 1 mM | 0 |

Ions of heavy metals as $Hg^{++}$ and $Ca^{++}$ inhibit the activity of C599 amylase, whereas neither PCMB, EDTA or Schardinger-cyclodextrins have any effect on the activity.

Cloning of the Maltogenic Amylase Gene from Bacillus C599

As described in further detail below, the maltogenic amylase gene can be cloned and expressed in *B. subtilis* in the following way:

Chromosomal DNA from C599 is partially degraded with restriction enzyme Mbol (Biolabs cat. No. 147). Fragments in the range of 4–12 kb are isolated and ligated (with DNA ligase (Biolabs Cat. No. 202)) with *E. coli* plasmid pACYC184 (Chang et al., J. Bacteriol. 134: 1141–56, 1978), which has been cut with restriction enzyme BamHl (Biolabs Cat. No. 136).

Plasmid pACYC184 confers resistance to both tetracyclin and chloramphenicol and contains a single restriction site for the restriction enzyme BamHl. Insertion of DNA in the BamHl site destroys the capacity to confer resistance to tetracyclin but not to chloramphenicol.

The ligation mixture is transformed into competent *E. coli* cells. The transformed cells are plated on an appropriate selective medium containing soluble starch and chloramphenicol. Chloramphenicol resistant transformants harbouring a cloned fragment in the BamHl site are identified as being tetracyclin sensitive. Among those, transformants exhibiting amylase activity are identified by the pale halo appearing around the colonies upon exposure of the starch containing agar to iodine vapour. One such transformant harbours a first recombinant plasmid containing a gene coding for the maltogenic amylase.

For subcloning into *B. subtilis* plasmid pBD64 (a derivative of *Staphylococcus aureus* plasmid pUB110 (Gryczan et al., J. Bacteriol. 141: 246–53, 1980)) is used. pBD64 is capable of replicating in *B. subtilis* and confers resistance to kanamycin and chloramphenicol.

pBD64 is cleaved with BamHl and ligated with the above prepared first recombinant plasmid partially cleaved with Sau3Al (Biolabs Cat. No. 169). This subcloning is preferably carried out by means of the so-called rescue technique (Gryczan et al., Mol.Gen.-Genet. 177: 459–67, 1980) using an amylase-negative *B. subtilis* strain harbouring plasmid pUB110, a plasmid from *Staphylococcus aureus* which can be transformed into *B. subtilis*.

Transformed cells of the pUB110 harbouring *B. subtilis* strain are then plated on an appropriate selective medium containing soluble starch and chloramphenicol. An Amy+ transformant harbouring a second recombinant plasmid is identified as above and plasmid from this transformant is isolated and transformed into an amylase-negative *Bacillus subtilis* which does not harbour pUB110. These transformed cells are then plated on an appropriate selective medium and Amy+ transformants harbouring the above second recombinant plasmid are identified.

The following examples are presented as illustrative embodiments of this invention and are not intended as specific limitations thereof.

EXAMPLE 1

Cloning of the maltogenic amylase gene from *B. subtilis* C599

A. Microorganisms and plasmids

All *Bacillus subtilis* strains were derivatives of *B. subtilis* 168 (Spizizen, Proc Natl. Acad. Sci. 44: 1072–78, 1958).

DN304: aroI906 sacA321 amy is a Met+ transformant of QB1133 (Steinmetz et al., Mol. Gen. Genet 148: 281–85, 1976) and has been deposited with the National Collection of Industrial Bacteria, Torry Research Station, Aberdeen, Scotland, on 7th March 1984 and accorded the reference number 11957. DN314 is DN304 pUB110 and DN311 is DN304 pBD64. Plasmids pUB110 and pBD64 (Gryczan et al., J.

Bacteriol. 134: 318–329 1978, and Gryczan et al., J. Bacteriol. 141: 246–53, 1980) were isolated from B. subtilis strains BD366 and BD624, respectively. pUB110 and pBD64 both confer resistance to kanamycin and pBD64 also to chloramphenicol. B. subtilis strains 168, QB1133, BD366 and BD624 can be obtained from the Bacillus Genetic Stock Center, Columbus, Ohio, USA (strain file number BGSC 1A1, 1A289, 1E6 and 1E22, respectively).

All Escherichia coli strains were derivatives of E. coli K-12. E. coli No. 802 met r⁻m+ gal lac (Wood, J.Mol.Biol. 16: 118–33 1966) and E. coli MC1000: Δ(ara-leu) 7697 ara D139 Δlac×74 gal K gal U str A (Casadaban et al., J.Mol.Biol. 138: 179–207, 1980) harbouring plasmid pACYC184 (Chang et al., J.Bacteriol. 134: 1141–56 1978) have both been deposited on 7th March, 1984 (NCIB No. 11958 NCIB No. 11956).

B. Transformation of E. coli

An overnight culture of E. coli K-12 strain No. 802 in LB (10 g Bacto tryptone, 5 g Bacto yeast extract and 10 g NaCl per liter water, pH 7.0) was diluted 100 fold in 500 ml LB and grown at 37° C. to $OD_{450}=0.4$. The culture was chilled, left 15 min. on ice spun for 15 min. at 3000 rpm (in a Sorvall GS3 rotor), resuspended in 200 ml cold 0.1M $CaCl_2$, left on ice for 20 min. spun for 10 min. at 3000 rpm, resuspended in 5 ml cold 0.1M $CaCl_2$ and left on ice for 20 hours. Cold glycerol was then added to 10% and aliquotes were frozen in liquid nitrogen and stored at −70° C. Frozen cells were thawn on ice, DNA was added, the mixture incubated 45 min. on ice, 2 min. at 37° C. and then plated on an appropriate selective medium.

C. Transformation of Bacillus subtilis

Competent Bacillus subtilis cells were prepared according to Yasbin et al. (J. Bacteriol. 121: 296–304, 1975). Cells were then harvested by centrifugation (7000 rpm, 3 min.), resuspended in one tenth volume of supernatant including 20% glycerol, frozen in liquid nitrogen and stored at −70° C. For transformation, frozen cells were thawed at 42° C. and mixed with one volume buffer (Spizizen's minimal medium (Spizizen, Proc. Natl. Acad. Sci. USA 44: 1072–78, 1958) with 0.4% glucose, 0.04M $MgCl_2$ and 0.002M EGTA). DNA was added and the mixture incubated with shaking at 37° C. for 20 min. Cells were then plated on appropriate selective media.

D. Preparation of plasmid pACYC184 from E. coli

E. coli K-12 strain MC1000 harbouring plasmid pACYC184 was grown over night in 250 ml LB, 0.4% glucose, 20 μg/ml chloramphenicol. Cells were harvested by centrifugation and resuspended in 4 ml Buffer 1 (0.025M Tris.HCl, pH=8.0, 0.01M EDTA, 0.05M glucose, 2 mg/ml lysozyme). The suspension was incubated at 0° C. for 15 min. and then mixed with 8 ml Buffer 2 (0.2M NaOH, 1% SDS). Then 6 ml Buffer 3 (3M NaAcetate, pH=4.8) was added, the mixture kept at 0° C. for 60 min. followed by centrifugation for 20 min. at 19000 rpm (ca. 45000 g in Sorvall SS34 rotor). The supernatant was precipitated with 0.6 vol cold isopropanol and resuspended in 1.2 ml 5TE (0.05M Tris.HCl, pH=8.0, 0.005M EDTA), plus 20 μl boiled RNase A (Boehringer) (2 mg/ml). 30 min. later the solution was layered on top of 4.0 ml Buffer 4 (80 g CsCl plus 56 ml 5TE) and 0.1 ml EtBr (ethidium bromide) in a VTi65 tube. The mixture was centrifuged at 45000 rpm for 20 h. The plasmid was then removed from the tube, dialyzed and extracted as described in section G.

E. Preparation of plasmid pBD64 from Bacillus subtilis DN311

Plasmid was prepared as described for E. coli strains (see section D) but with the following modifications. Growth was in LB including 0.01M potassium phosphate, pH=7.0 and 6 μg/ml chloramphenicol. After harvest, cells were incubated at 37° C. with lysozyme. Buffer 2 was replaced by a mixture of one volume Buffer 2 and three volumes Buffer 5 (0.2M glycine, 0.2M NaCl and 1% SDS). The following steps were the same as in D.

F. Small scale preparation of plasmids from B. subtilis

Plasmid from 5 ml B. subtilis in LB (including 0.01M phosphate pH=7.0 and appropriate antibiotics) was prepared as in section E except: 1: volumes of buffers were reduced four fold. 2: 0.5 ml phenol and 0.5 ml chloroform are added after Buffer 3. 3: After centrifugation at 19000 rpm, the supernatant was precipitated with ethanol, resuspended in 400 μl Buffer 6 (0.05M Tris.HCl pH=8.0, 0.1M NaAcetate), the plasmid was again precipitated, resuspended in 400 μl Buffer 6, precipitated, washed and resuspended in 100 μl TE with 1 μg/ml boiled RNase A (Boehringer).

G. Preparation of chromosomal DNA from Bacillus C599

A pellet of frozen cells from about 50 ml culture was resuspended in 1.1 ml Buffer (0.05M Tris.HCl, pH=7.4, 0.1M NaCl, 25% sucrose). 100 μl lyzosyme (25 mg/ml) and 150 μl EDTA (0.5M, pH=8.0) were added. The mixture was incubated at 37° C. for 30 min. 2 ml 0.2% SDS was added followed by incubation for 30 min. at 37° C. 1 g CsCl and 0.05 ml EtBr (10 mg/ml) were added per 0.95 ml mixture and the mixture was centrifuged at 45000 rpm, 15° C., for 20 hours in a VTi65 rotor (Beckman).

The DNA was located under a long wave UV lamp and removed by puncturing the tube with a syringe. EtBr was extracted with isopropanol and the solution dialyzed for 2 hours against TEE (0.01M Tris.HCl, pH=8.0, 0.01M EDTA). The solution was then adjusted to 8 ml with TEE and extracted twice with phenol and once with chloroform. The DNA was precipitated with 0.1M NaCl and cold ethanol and dissolved in 1 ml TE (0.01M Tris.HCl, pH=8.0, 0.001M EDTA). The solution of chromosomal DNA (chr DNA) was kept at 4° C.

H. Partial cutting and fractionation of chr DNA from Bacillus C599

60 μg chr DNA from C599 (see section G) was cut in 900 μl buffer (0.01M Tris.HCl, pH=7.4, 0.075M NaCl, 0.01M $MgCl_2$, 0.006M mercaptoethanol, 100 μg/ml gelatine) with 10 units MboI (Biolabs Cat. No. 147) at 37° C. After 10 min. and 40 min., 450 μl samples were extracted with phenol, precipitated with 0.1M NaCl and cold ethanol. Each sample was dissolved in 100 μl TEE. 100 μl DNA was loaded per 12 ml sucrose gradient (Maniatis T. et al., Cell 15: 687–701, 1978) and centrifuged at 27000 rpm for 22 hours at 20° C. in a SW41 rotor (Beckman).

0.5 ml fractions were tapped after puncturing the bottom of the tube and precipitated with cold ethanol. The DNA was dissolved in 50 μl TE and the size of the DNA in each fraction estimated on a 0.7% agarose gel stained with 0.5 μg/ml EtBr. Fractions containing DNA from about 4–12 kb were pooled, phenol extracted, ethanol precipitated and dissolved in TE.

I. Isolation of recombinant plasmid containing an amylase gene

4 μg pACYC184 (see section D) was cut with 8 U BamHl (Biolabs Cat. No. 136) for 1 hour, 37° C. in 50 μl buffer (0.006M Tris.HCl, pH=8.0, 0.15M NaCl, 0.006M MgCl₂, 0.006M mercaptoethanol, 100 μg/ml gelatine). The linear DNA was treated with calf intestine alkaline phosphatase (Sigma P 4502), (Goodman et al., Methods in Enzymology, 68: 75–90, 1979). 0.4 μg BamHl and phosphatase treated pACYC184 was then ligated with ca. 1 μg C599 chr DNA from sucrose gradients with about 100 U DNA ligase (Biolabs Cat. No. 202) for 4 hours, 16° C. in 100 μl buffer (0.066M Tris.HCl, pH=7.5, 0.01M MgCl₂, 25 μg/ml gelatine, 0.001M ATP, 0.01M DTT). The ligated DNA was transformed into competent E. coli strain No. 802 as described in section B.

The cells were plated on freshly poured agar plates consisting of two layers: At the bottom, 10 ml LB agar with 0.5% soluble starch and 60 μg/ml chloramphenicol. At the top 25 ml of the same agar but without chloramphenicol. After incubation overnight at 37° C., about 1200 chloramphenicol resistant transformants appeared. Approx. 600 of these were tetracycline sensitive indicating that the plasmid of these transformants harboured a cloned fragment in the BamHl site. Among those 600 colonies (representing a gene bank of C599) one strain, named DN400, exhibited amylase activity as indicated by the pale halo appearing around this colony upon exposure of the starch containing agar to vapour of iodine. Strain DN400 was shown to harbour a plasmid, named pDN400, of approx. 14000 basepairs including the amylase coding gene.

J. Subcloning of pDN400 in *Bacillus subtilis*

About 1 μg of pDN400 (constructed as described in section I and prepared from E. coli strain DN400 as described for pACYC184 in section D) was cut at 37° C. in 100 μl buffer (0.006M Tris.HCl, pH=7.5, 0.05M NaCl, 0.005M magnesium chloride, 100 μg/ml gelatine) with 0.06 U Sau3Al (Biolabs cat. No. 169). 25 μl aliquotes were transferred to phenol after 10, 20, 30 and 40 min and were phenolextracted and precipitated with 0.1M NaCl and cold ethanol. Half of the DNA was ligated (see section H) with 0.4 μg plasmid pBD64 (see section E), which had been cut with BamHl (as described for pACYC184 in section I).

A *Bacillus subtilis* strain named DN314 was then transformed (see section C) with the ligation mixture and plated on LB agar plates containing 0.01M potassium phosphate pH=7.0, 0.5% soluble starch and 6 μg/ml chloramphenicol. Among ca. 6000 transformants one Amy⁺ (starch-degrading as tested with iodine) was identified.

Plasmid from this strain was isolated (as described in section F) and transformed into *Bacillus subtilis* strain, named DN304, (as described in section C). One Amy⁺ transformant strain, named DN463, harbouring plasmid pDN452 was isolated. As described in the following Example 2 cultivating of DN463 provided improved yields of the thermostable amylase product according to the present invention.

EXAMPLE 2

Preparation of the thermostable, maltogenic amylase from *Bacillus subtilis* strain DN463

A culture of the above cloned microorganism DN463 was inoculated in 500 ml shake flasks on 100 ml of the following substrate:
Liquefied starch: 12,5% w/v (tap water),
Soy meal: 7,5%,
Na₂HPO₄: 1%.

5 μg/ml chloramphenicol was added to the above substrate before the inoculation.

Incubation was performed at 30° C. for 3–4 days.

The culture broth was centrifugated for 20 min at 6000 g. The centrifugate containing about 200 U/ml was used directly in the following example.

EXAMPLE 3

Substrates for saccharification were prepared by redissolving a 7DE spray-dried maltodextrin in deionized water and making up to approximately 30% D.S. The saccharification experiments were carried out in standard 500 ml laboratory batch reactors. Aliquots of this substrates were heated to 60° C. and the pH adjusted to 5.5 and from the amylase product of example 2.50 amylase units/g D.S. were then added. After 72 hours at 60° C. the content of glucose, maltose and maltotriose in the syrup was as follows:
glucose: 5%,
maltose: 67%,
maltotriose: 0%.

Saccharification with 25 β-amylase unit/g D.S. Biozym MII (soy bean β-amylase, 20.000 β-amylase/g) under the same conditions gives a syrup containing 0.3% glucose, 61% maltose and 7% maltotriose.

We claim:

1. A process for preparing a maltogenic amylase enzyme wherein a transformed host microorganism containing the gene coding for the maltogenic amylase produced by Bacillus strain NCIB 11837 is cultivated in a suitable nutrient medium containing carbon and nitrogen sources and inorganic salts followed by recovery of the maltogenic amylase enzyme from the culture broth.

2. A process according to claim 1 wherein the host microorganism is a *Bacillus subtilis*.

3. A process according to claim 2 wherein the host organism is *Bacillus subtilis* strain 168 or mutants or variants thereof.

4. A process according to claim 1 wherein the donor microorganisms is Bacillus strain NCIB 11837.

5. A process for producing a recombinant plasmid containing the gene coding for the maltogenic amylase produced by Bacillus strain NCIB 11837 comprising cutting chromosomal DNA from a donor microorganism productive of said amylase with an appropriate restriction enzyme to obtain a linear DNA-sequence containing the amylase coding gene, cutting a suitable vector with an appropriate restriction enzyme to obtain a second linear DNA-sequence and ligating the linear DNA-sequences to obtain a recombinant plasmid containing the amylase gene.

6. A process according to claim 5, wherein the donor microorganism is Bacillus strain NCIB 11837.

7. A process according to claim 5, wherein the vector is a *E. coli* plasmid.

8. A process according to claim 7, wherein the *E. coli* plasmid is pACYC184.

9. A process according to claim 5 further comprising ligation of the maltogenic amylase gene from the said recombinant plasmid with a plasmid able to replicate in a *Bacillus subtilis* host.

10. A process according to claim 9 wherein the plasmid enabling replication in *Bacillus subtilis* is plasmid pBD64 or pUB110 or a derivative of one of said plasmids.

11. A process according to claim 5 comprising cutting chromosomal DNA from Bacillus strain NCIB 11837 with the restriction enzyme Mbol, isolating DNA-fragments in the range of 4–12 kb, ligating with *E. coli* plasmid pACYC184, transforming into *E. coli* cells, identifying starch degrading transformants habouring plasmids containing the amylase gene, cutting said plasmids with restriction enzyme Sau3A1 and ligating with plasmid pBD64 which has been cut with the restriction enzyme BamH1.

12. A recombinant plasmid containing the gene coding for the maltogenic amylase produced by Bacillus strain NCIB 11837.

13. The recombinant plasmid according to claim 12 further comprising at least the partial nucleotide sequence of plasmid pBD64 or pUB110 or derivatives thereof and the DNA sequence coding for said maltogenic amylase.

14. The recombinant plasmid of claim 13 further comprising the plasmid illustrated in FIG. 3 hereof.

* * * * *